(12) United States Patent
Atkinson

(10) Patent No.: US 8,466,414 B2
(45) Date of Patent: *Jun. 18, 2013

(54) ION MOBILITY SPECTROMETERS

(75) Inventor: Jonathan Richard Atkinson, Watford (GB)

(73) Assignee: Smiths Detection-Watford Limited, Watford, Hertfordshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/209,824

(22) Filed: Aug. 15, 2011

(65) Prior Publication Data

US 2011/0300638 A1 Dec. 8, 2011

Related U.S. Application Data

(63) Continuation of application No. 12/529,238, filed on Aug. 31, 2009, now Pat. No. 7,999,224.

(30) Foreign Application Priority Data

Mar. 9, 2007 (GB) .................................. 0704547.9

(51) Int. Cl.
*H01J 49/00* (2006.01)

(52) U.S. Cl.
USPC ........... 250/290; 250/281; 250/282; 250/288; 250/292

(58) Field of Classification Search
USPC .................. 250/281, 282, 285–288, 290, 292
See application file for complete search history.

(56) References Cited

U.S. PATENT DOCUMENTS

| 7,820,962 B2 | 10/2010 | Wynn et al. |
| 7,999,224 B2 * | 8/2011 | Atkinson ..................... 250/292 |
| 2005/0133710 A1 | 6/2005 | Losch et al. |
| 2009/0174412 A1 | 7/2009 | Atkinson et al. |
| 2010/0230588 A1 | 9/2010 | Atkinson et al. |

FOREIGN PATENT DOCUMENTS

| WO | 0079261 | 12/2000 |
| WO | 03104763 | 12/2003 |
| WO | 2006114580 | 11/2006 |

* cited by examiner

*Primary Examiner* — Michael Maskell
(74) *Attorney, Agent, or Firm* — Reinhart Boerner Van Deuren S.C.

(57) ABSTRACT

An ion mobility spectrometer has a reaction region separated from a drift region by an electrostatic gate. A doping circuit supplies a dopant to the reaction region but the drift region is undoped. Two high field ion modifiers are located one after the other in the drift region. One ion modifier can be turned on to remove dopant adducts from the admitted ions, or both ion modifiers can be turned on so that the ions are also fragmented. In this way, several different responses can be produced to provide additional information about the nature of the analyte substance and distinguish it from interferents.

23 Claims, 1 Drawing Sheet

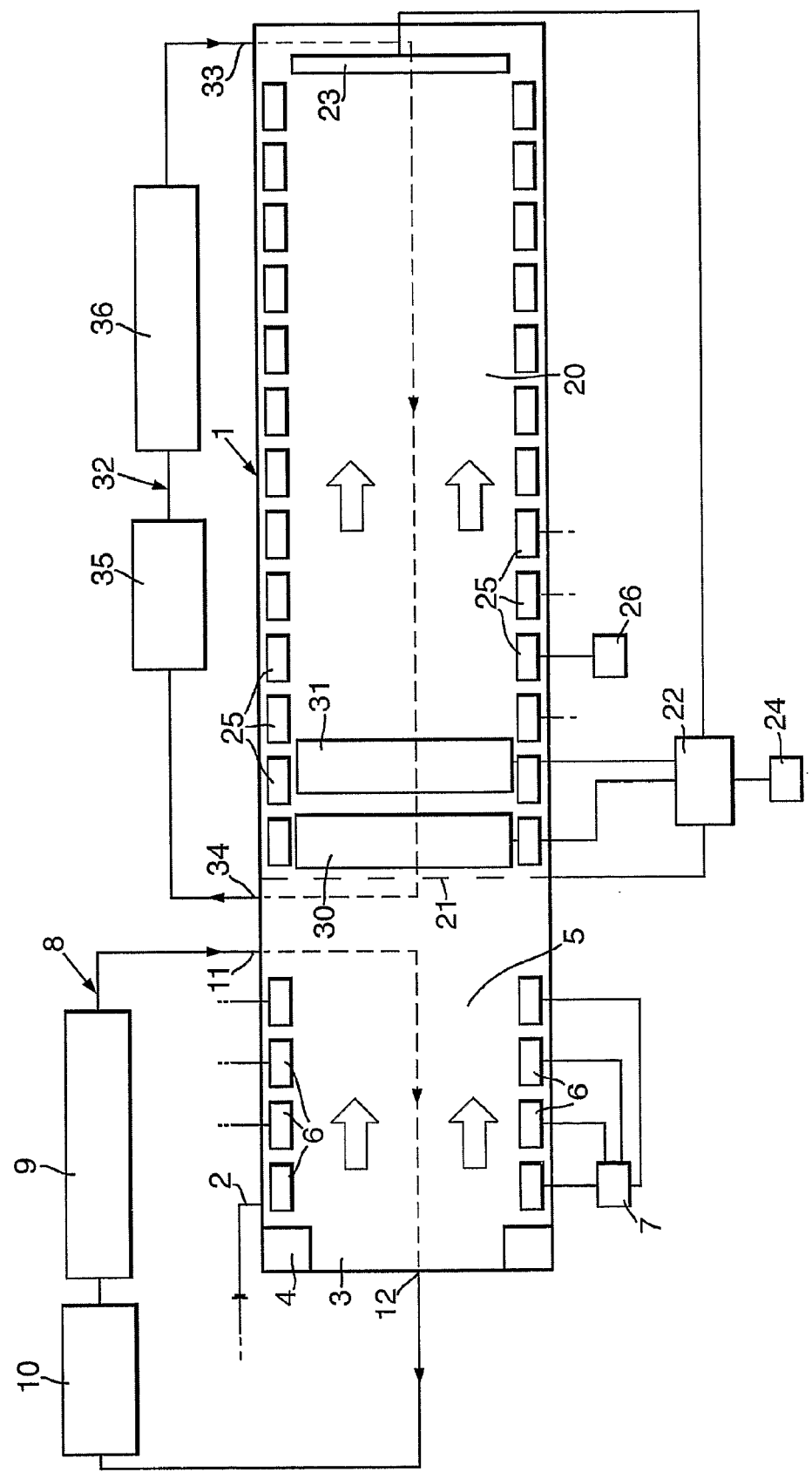

ION MOBILITY SPECTROMETERS

CROSS REFERENCE TO RELATED APPLICATION

This patent application is a continuation of U.S. patent application Ser. No. 12/529,238, filed on Aug. 31, 2009, now U.S. Pat. No. 7,999,224, issued on Aug. 16, 2011, entitled "Ion Mobility Spectrometers," which patent application is assigned to the assignee of the present invention and which patent application is hereby incorporated herein by reference in their entirety.

BACKGROUND OF THE INVENTION

Field of the Invention

This invention related to ion mobility spectrometers of the kind having a drift region and a reaction region.

Ion mobility analysis is a commonly used technique for detecting the presence of explosives, hazardous chemicals, and other vapors. An ion mobility spectrometer (IMS) typically includes a detector cell to which a sample of air containing a suspected substance or analyte is continuously supplied as a gas or vapor. The cell operates at or near atmospheric pressure and contains electrodes energized to produce a voltage gradient along the cell. Molecules in the sample of air are ionized, such as by means of a radioactive source, an ultraviolet (UV) source, or by corona discharge, and the ionized molecules are admitted into the drift region of the cell by an electrostatic gate at one end. The ionized molecules drift to the opposite end of the cell at a speed that is dependent upon the mobility of the ion. By measuring the time of flight along the cell, it is possible to identify the ion.

In an undoped IMS system, it has been found that certain nerve agents produce identifiable breakdown peaks when subject to ion modification by a high electrical field. This leads to an increase in the information that can be gained from the spectrum and leads to a greater confidence in analyte detection.

It is common practice to improve detection by adding a dopant substance to the analyte substance in order to distinguish between an interferent substance producing a similar spectral output. The dopant is selected to combine with the substance of interest so that an identifiable pair of spectral peaks are respectively produced by the undoped analyte substance and the doped analyte substance. The dopant is also selected so that it does not combine with the interferent substance, or it combines in a manner that produces a readily distinguishable output different from the substance of interest.

It has been found that ion modification is not possible in a doped system. Instead, the ion modification process removes the dopant adducts from certain ions without producing any modification of the ion itself. This may be because the dopant adduct is only removed from the ions when it has passed most of the way through the modifier, and there is insufficient distance left in the modifier for further ion modification to take place. De-adducted ions will only remain this way if the region of the ion modifier is free of dopant, since otherwise recombination will occur.

It is accordingly desirable to provide an alternative ion mobility spectrometer.

SUMMARY OF THE INVENTION

According to one aspect of the present invention there is provided an ion mobility spectrometer of the above-specified kind, characterized in that the spectrometer is arranged and configured to dope the reaction region without doping the drift region, wherein the spectrometer includes at least two selectively operable ion modifiers located one after the other along the ion flow path such that at least one modifier is effective when operated to remove dopant adducts from the ions.

At least one of the ion modifiers is preferably arranged to establish a high electrical field sufficient to fragment the ions. Alternatively, at least one of the ion modifiers may be effective to raise the temperature to a level sufficient to fragment the ions. The spectrometer preferably includes a filtered gas flow path flowing through the drift region to remove any dopant from the drift region. The spectrometer may include a doping circuit arranged to supply a dopant vapor to a region of the reaction region adjacent the drift region and to remove the dopant vapor at the opposite end of the reaction region such that the dopant flows away from the drift region. The spectrometer may include an electrostatic gate between the reaction region and the drift region. The spectrometer may be arranged to operate the ion modifiers in response to detection of a peak corresponding to a known interferent such that dopant adducts are then removed. The spectrometer may be arranged to derive a first output when both ion modifiers are off, a second output when one ion modifier only is on, and a third output when both ion modifiers are on.

DESCRIPTION OF THE DRAWINGS

An ion mobility spectrometer that is constructed and operated according to the present invention will now be described, by way of example, with reference to the accompanying drawing, which is a schematic diagram of an exemplary ion mobility spectrometer.

DETAILED DESCRIPTION OF THE PREFERRED EMBODIMENT

The spectrometer has a tubular drift cell 1 with an inlet 2 at its left-hand end (as shown in the FIGURE) by which a sample analyte gas or vapor enters the drift cell 1 via a selective barrier such as a membrane, pinhole, or the like (not shown). The inlet 2 opens into an ionization region 3 in the drift cell 1 that includes a conventional ionization source 4, such as a corona ionization point, a radioactive source, a UV photoionization source, or the like. The ionization region 3 opens into a reaction region 5 in which ions produced by the ionization source 4 react with the analyte molecules.

The reaction region 5 includes several electrode pairs 6 spaced along the region and driven by a voltage source 7 to produce a potential gradient along the region that draws ions to the right. The reaction region 5 is connected into a doping circuit 8 including a conventional dopant source 9 and a pump 10. The outlet 11 of the doping circuit 8 is connected to the drift cell 1 at the right-hand end of the reaction region 5 (as shown in the FIGURE); its inlet 12 is connected to the left-hand end of the reaction region 5 (as shown in the FIGURE) so that dopant gas flows along the reaction region 5 from the right to the left (as shown in the FIGURE).

The right-hand end of the reaction region 5 (as shown in the FIGURE) communicates with a drift region 20 via a conventional electrostatic gate 21 by which ions from the reaction region 5 are admitted into or excluded from the drift region 20. Operation of the electrostatic gate 21 is controlled by a processing and control unit 22. The drift region 20 includes an ion detector or collector plate 23, the output of which is connected with an input to the processing and control unit 22 so as to produce an output spectrum representative of the ions incident on the collector plate 23, in the usual way.

The output of the processing and control unit 22 is supplied to a display 24 or other utilization element. Electrode pairs 25 spaced along the drift region 20 are connected to a voltage source 26 to provide a potential gradient along the length of the drift region 20 that is effective to draw the ions from left to right (as shown in the FIGURE) towards the collector plate 23.

Immediately adjacent the electrostatic gate 21 inside the drift region 20 are mounted two ion modifier grids 30 and 31, each in the form of a pair of parallel electrode grids extending laterally of the ion flow path, which ion flow path extends axially along the drift cell 1. The construction of the ion modifier grids 30 and 31 is such as to allow ions to pass freely through them and, in this respect, the ion modifier grids are preferably made from a mesh of electrically conductive wires with spaces between them through which the ions can flow. The ion modifier grids 30 and 31 are connected to the processing and control unit 22, which is operable to apply a high voltage between the ion modifier grids 30 and 31 that is sufficient to modify the nature of any ions in the space between the ion modifier grids 30 and 31, such as by fragmentation of the ions. An additional effect of this high field is to remove the dopant adducts from the ions.

Alternative ion modifiers may be possible, and may involve heating, radiation, electrical discharge, magnetic fields, or lasers. Although the ion modifier grids 30 and 31 are shown as being close to each other, they could be spaced from each other, with the downstream, right-hand (as shown in the FIGURE) ion modifier grid 31 being located a distance along the drift region 20.

Clean dry air is circulated along the drift region 20 by an air flow system 32 having an outlet 33 into the drift cell 1 adjacent the collector plate 23. The inlet 34 of the air flow system 32 is located just to the left of the electrostatic gate 21 (as shown in the FIGURE). The air flow system 32 includes a pump 35 and a filter in the form of a molecular sieve 36 connected in series between the inlet 34 and the outlet 33. Air is, therefore, circulated to flow from right to left along the drift region 20 (as shown in the FIGURE) and is dried and cleaned by the action of the molecular sieve 36. The air flow system 32 is effective to remove any dopant vapor that might permeate into it from the reaction region 5. In this way, the reaction region 5 is doped and the drift region 20 is undoped.

In operation, analyte sample vapor is admitted to the drift cell 1 via the inlet 2 and is doped and ionized in the reaction chamber 5. The resultant ions are then moved by the field established by the electrode pairs 6 towards the electrostatic gate 21. The doped ions are admitted in a timed fashion by the electrostatic gate 21 under control of the processing and control unit 22 and enter the drift region 20.

In normal operation, with the ion modifier grids 30 and 31 being unenergized and inoperative, the doped ions move along the drift region 20 to the collector plate 23 and produce corresponding responses at the processing and control unit 22. If, however, the output from the processing and control unit 22 includes a peak for which there is a known interferent, both ion modifier grids 30 and 31 are turned on to render them operative. The effect of this is that the upstream, left-hand (as shown in the FIGURE) ion modifier grid 30 removes any dopant adduct from the ions passing through it.

The now undoped, ions pass to the downstream modifier 31, where they are further modified to cause fragmentation or other changes in the ion chemistry of the ions. Because the drift region 20 is undoped, the undoped and modified ions move along the drift region 20 without being exposed to any dopant. This causes a change in the output response at the collector plate 23 so that the response produced by the analyte substance of interest and its interferent will generally be different when the ion modifier grids 30 and 31 are turned on. By characterizing the apparatus before use with the analyte substance and its interferent, it is, therefore, possible to distinguish between the substance of interest and its interferent.

The system could be arranged such that the output of the collector plate 23 is monitored initially with only one ion modifier grid 30 operative so that the only change was the removal of the dopant adducts. Then, the second ion modifier grid 31 could be turned on. In this way, three different outputs would be produced: one output derived from doped ions, with neither modifier on; a second output derived from undoped, unmodified ions, with one modifier on; and a third output derived from undoped, modified ions, with both ion modifiers on.

It will be appreciated that the ion mobility spectrometer of the present invention could also have more than two ion modifiers.

Although the foregoing description of the ion mobility spectrometer of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. An ion mobility spectrometer comprising:
   a drift region;
   a reaction region, wherein the spectrometer is configured to dope the reaction region without doping the drift region; and
   an ion modifier element located along the ion flow path so the ion modifier element is effective when operated to undope and/or modify the ions.

2. An ion mobility spectrometer as defined in claim 1, wherein the ion modifier element is configured to remove a dopant adduct from an ion.

3. An ion mobility spectrometer as defined in claim 1, wherein the ion modifier element is configured to establish an electrical field that is sufficiently high to fragment the ions.

4. An ion mobility spectrometer as defined in claim 1, wherein the ion modifier element comprises:
   at least two selectively operable ion modifiers located one after the other along the ion flow path.

5. An ion mobility spectrometer as defined in claim 4, wherein at least one of the ion modifiers is effective to raise at least some of the ion's temperature sufficiently high to cause said ions to fragment.

6. An ion mobility spectrometer as defined in claim 1, wherein the ion mobility spectrometer is additionally configured to flow filtered gas through the drift region to remove dopant.

7. An ion mobility spectrometer as defined in claim 1, additionally comprising:
a doping circuit arranged to supply a dopant at an end of the reaction region adjacent the drift region and to remove the dopant vapor at the opposite end of the reaction region so the dopant flows away from the drift region.

8. An ion mobility spectrometer as defined in claim 1, additionally comprising:
an electrostatic gate between the reaction region and the drift region.

9. An ion mobility spectrometer as defined in claim 1, wherein the ion mobility spectrometer is configured to operate the ion modifier element in response to detection of a peak corresponding to a known interferent to remove dopant adducts.

10. An ion mobility spectrometer as defined in claim 1, wherein the ion mobility spectrometer is configured to derive a first output when the ion modifier element is operated in a first mode, a second output when the ion modifier element is operated in a second mode, and a third output when the ion modifier element is operated in a third mode.

11. An ion mobility spectrometer as defined in claim 1, additionally comprising:
an arrangement to establish a voltage gradient in the reaction region to draw ions towards the drift region.

12. An ion mobility spectrometer as defined in claim 1, additionally comprising:
an arrangement to establish a voltage gradient in the drift region to draw ions from adjacent the reaction region to the drift region's end opposite the reaction region.

13. An ion mobility spectrometer as defined in claim 1, additionally comprising:
a detection apparatus located near said second end of said drift chamber and providing an output indicative of ions detected by said detection apparatus.

14. An ion mobility spectrometer comprising:
a drift region;
a reaction region, wherein the spectrometer is configured to dope the reaction region without doping the drift region; and
an ion modifier element, located along an ion flow path, selectably operable in two different modes, wherein subsequent to operation in a first mode that causes the ion mobility spectrometer to produce a first result the ion modifier element is configured to operate in at least an other mode to produce at least one other result.

15. An ion mobility spectrometer as defined in claim 14, wherein the ion modifier element is selectively operable in three modes, that result in the ion mobility spectrometer providing a different output.

16. An ion mobility spectrometer as defined in claim 14, wherein the ion modifier element comprises:
two or more selectively operable ion modifiers located one after the other along the ion flow path.

17. An ion mobility spectrometer as defined in claim 16, wherein one of the ion modifiers is arranged to remove dopant adducts from the ions.

18. An ion mobility spectrometer as defined in claim 16, wherein one of the ion modifiers is arranged to modify the ions.

19. An ion mobility spectrometer as defined in claim 14, wherein the ion mobility spectrometer is additionally configured to flow filtered gas through the drift region to remove dopant.

20. An ion mobility spectrometer as defined in claim 14, additionally comprising:
a doping circuit arranged to supply a dopant to the reaction region adjacent the drift region so the dopant flows away from the drift region and to remove the dopant at an opposite end of the reaction region.

21. An ion mobility spectrometer as defined in claim 14, additionally comprising:
an electrostatic gate between the reaction region and the drift region.

22. A method comprising:
doping a reaction region of an ion mobility spectrometer without doping a drift region of the ion mobility spectrometer; and
selectively operating two or more ion modifiers located one after the other along the ion flow path so at least one ion modifier is effective when operated to remove dopant adducts from the ions.

23. A method comprising:
doping a reaction region of an ion mobility spectrometer without doping a drift region of the ion mobility spectrometer; and
selectively operating an ion modifier element located along an ion flow path so the ion modifier element is effective when operated to undope and/or chemically modify the ions.

* * * * *

UNITED STATES PATENT AND TRADEMARK OFFICE
CERTIFICATE OF CORRECTION

PATENT NO. : 8,466,414 B2  
APPLICATION NO. : 13/209824  
DATED : June 18, 2013  
INVENTOR(S) : Jonathan Richard Atkinson It is certified that error appears in the above-identified patent and that said Letters Patent is hereby corrected as shown below:

On the Title Page, Item (63) Related U.S. application Data:

"Continuation of application No. 12/529,238, filed on Aug. 31, 2009, now Pat. No. 7,999,224" should read --Continuation of application No. 12/529,238, filed as application No. PCT/GB2008/000759 on Mar. 6, 2008, now Pat. No. 7,999,224.--

In the Specification, In the Cross Reference To Related Application:
Column 1, lines 6-12

"This patent application is a continuation of U.S. patent application Ser. No. 12/529,238, filed on Aug. 31, 2009, now U.S. Pat. No. 7,999,224, issued on Aug. 16, 2011, entitled 'Ion Mobility Spectrometers,' which patent application is assigned to the assignee of the present invention and which patent application is hereby incorporated herein by reference in their entirety." should read --This patent application is a continuation of U.S. patent application Ser. No. 12/529,238, which is the National Stage of International Application No. PCT/GB2008/000759, filed Mar. 6, 2008, which claims priority to GB 0704547.9, filed March 9, 2007, each of which patent applications are hereby incorporated herein by reference in their entireties.--

Signed and Sealed this  
Sixth Day of May, 2014

Michelle K. Lee  
*Deputy Director of the United States Patent and Trademark Office*